(12) United States Patent
Urbanek

(10) Patent No.: US 9,314,320 B2
(45) Date of Patent: Apr. 19, 2016

(54) DEVICE FOR MITIGATION OF TEMPOROMANDIBULAR JOINT DISORDER

(75) Inventor: Anthony Phillip Urbanek, Brentwood, TN (US)

(73) Assignee: TMJ Services LLC, Franklin, TN (US)

(*) Notice: Subject to any disclaimer, the term of this patent is extended or adjusted under 35 U.S.C. 154(b) by 70 days.

(21) Appl. No.: 13/317,487

(22) Filed: Oct. 19, 2011

(65) Prior Publication Data

US 2013/0098375 A1 Apr. 25, 2013

(51) Int. Cl.

| | | |
|---|---|---|
| *A61F 5/37* | (2006.01) | |
| *A61B 19/08* | (2006.01) | |
| *A61C 5/14* | (2006.01) | |
| *A61C 3/00* | (2006.01) | |
| *A61C 19/04* | (2006.01) | |
| *A61C 5/00* | (2006.01) | |
| *A61C 5/08* | (2006.01) | |
| *A61C 19/06* | (2006.01) | |
| *A63B 71/08* | (2006.01) | |
| *A61F 5/56* | (2006.01) | |
| *A61C 7/00* | (2006.01) | |
| *A61C 7/08* | (2006.01) | |
| *A61F 5/00* | (2006.01) | |

(52) U.S. Cl.
CPC . *A61C 19/06* (2013.01); *A61C 7/00* (2013.01); *A61C 7/08* (2013.01); *A61F 5/00* (2013.01); *A61F 5/56* (2013.01); *A63B 71/08* (2013.01); *A63B 71/085* (2013.01); *A61F 2005/563* (2013.01)

(58) Field of Classification Search
CPC ...... A63B 70/00; A63B 71/08; A63B 71/085; A61F 5/00; A61F 5/56; A61F 5/66; A61C 7/00; A61C 7/08

USPC ........... 128/846, 857–863; 433/6, 18, 68, 69, 433/140, 225

See application file for complete search history.

(56) References Cited

U.S. PATENT DOCUMENTS

| | | | | |
|---|---|---|---|---|
| 3,991,471 A | * | 11/1976 | Hoops | ........................ 433/167 |
| 4,211,008 A | | 7/1980 | Lerman | |
| 4,568,280 A | | 2/1986 | Ahlin | |
| 4,773,853 A | | 9/1988 | Kussick | |
| 4,810,192 A | | 3/1989 | Williams | |
| 5,066,226 A | | 11/1991 | Summer | |
| 5,085,584 A | * | 2/1992 | Boyd | ............................ 433/6 |
| 5,173,048 A | | 12/1992 | Summer | |
| 5,203,701 A | | 4/1993 | Burtch | |
| 5,368,477 A | | 11/1994 | Neely | |
| 5,511,562 A | | 4/1996 | Hancock | |
| 5,584,687 A | | 12/1996 | Sullivan et al. | |
| 5,879,155 A | | 3/1999 | Kittelson | |
| 5,899,691 A | | 5/1999 | Parker et al. | |
| 6,237,601 B1 | | 5/2001 | Kittelson et al. | |
| 6,978,786 B2 | | 12/2005 | Sabbagh | |
| 7,234,467 B2 | | 6/2007 | Ball | |
| 7,607,438 B2 | | 10/2009 | Pelerin | |
| 7,730,891 B2 | * | 6/2010 | Lamberg | ..................... 128/848 |
| 2009/0241971 A1 | | 10/2009 | Eubank | |

FOREIGN PATENT DOCUMENTS

| | | |
|---|---|---|
| EP | 1663049 | 12/2010 |
| JP | 2009082670 A | 4/2009 |

* cited by examiner

*Primary Examiner* — Alireza Nia
*Assistant Examiner* — Brandon L Jackson
(74) *Attorney, Agent, or Firm* — Nicolo Davidson; Waller Lansden Dortch & Davis, LLP

(57) ABSTRACT

A device for mitigation of temporomandibular joint disorder with lingual tooth surface contact surface, hard palate conformity, anterior pad, and pad wings.

14 Claims, 4 Drawing Sheets

DEVICE FOR MITIGATION OF TEMPOROMANDIBULAR JOINT DISORDER

CROSS REFERENCE TO RELATED APPLICATIONS

Not Applicable

STATEMENT REGARDING FEDERALLY SPONSORED RESEARCH OR DEVELOPMENT

Not Applicable

DESCRIPTION OF ATTACHED APPENDIX

Not Applicable

BACKGROUND OF THE INVENTION

This invention relates generally to the field of dental appliances and more specifically to a device for mitigation of temporomandibular joint disorder. The temporomandibular joint is the joint between the mandible, lower jaw, and the skull, particularly at a portion of the temporal bone.

The joint allows rotary motion of the jaw and translational motion, side to side, of the mandible, which allows a variety of functions involving lower jaw movement. As are all joints, the temporomandibular joint is susceptible to dysfunctions of various sorts.

In example, such common anomalies as bruxism, (repetitive unconscious clenching or grinding of teeth, often during sleep), malalignment of the occlusal surfaces of the teeth, jaw thrusting, degenerative joint disease, or insufficient overbite can cause excess stress on the temporomandibular joint. Said stress may cause damage to joint elements causing undesirable effects such as biting or chewing difficulty or discomfort, clicking, popping, or grating sound accompanying jaw movement, dull, aching pain in the face, earache, headache including migraine, hearing loss, jaw pain, reduced ability to open and close mouth, tinnitus, and neck and shoulder pain. Said symptoms may be referred to generically as temporomandibular joint disorder.

Remedies for temporomandibular joint disorder include analgesic drugs of various sorts, manual adjustment of the teeth by grinding, reconstructive dentistry, orthodontics, arthrocentisis, surgical repositioning of jaws, replacement of the jaw joints with implants, muscle relaxation therapy, and hypnotherapy, among others. While such therapies can yield satisfactory results, they can be expensive, radically invasive, painful and otherwise uncomfortable. They may require extended periods of time during which no relief of symptoms is realized. Thus they are generally considered undesirable, especially if relatively inexpensive and non-invasive alternatives are available. Occlusal splints, or dental appliances, comprise such alternatives. The instant art is a novel and counterintuitive advancement in the art thereof.

Occlusal splints for the mitigation of temporomandibular joint disorder are known and in use.

In example, U.S. Pat. No. 7,607,438 B2 by Pelerin discloses a mouth guard having a tray dimensioned to receive at least the two front incisors, said trough having an impression material. A piece is molded which fits over at least the two aforesaid teeth.

The instant art has no tray and no moldable material. Further, it engages only lingual surfaces of upper anterior teeth. It does not engage any facial tooth surfaces, but engages only occlusal surfaces of anterior mandibular teeth.

U.S. Pat. No. 4,773,853 by Kussick recites a single appliance having a pair of spaced apart segments extending downwardly and posteriorly from an element held in place by covering the facial, lingual, and occlusal surfaces of the anterior dentition of the upper jaw to engage lingual surfaces of selected teeth on the mandibular arch.

The instant art does not engage facial surfaces of upper jaw and has no downwardly and posteriorly extending projections from the upper jaw teeth engaging element and engages only the occlusal surfaces of lower jaw anterior teeth.

U.S. Pat. No. 5,511,562 by Hancock teaches a dental appliance comprising a U-shaped channel member having an inner and outer wall with connectors dividing the appliance into upper and lower compartments containing a pliable substance which engages the upper and lower teeth.

The instant art recites no channels having walls and no upper and lower compartments.

U.S. Pat. No. 5,203,701 by Burtch teaches an interoral appliance having upper and lower members which fit on the upper and lower teeth. The lower member has an upward projection which engages the upper member.

The instant art comprises no lower member and no projections from one member to another. He instant art engages only lingual surfaces of upper teeth and only occlusal surfaces of lower teeth.

U.S. Pat. No. 4,568,280 by Ahlin recites a dental appliance having a dental arch defined by inner and outer walls and an interconnecting web for channels to receive dental arches.

The instant art recites no inner and outer walls, no interconnecting web, and no channels to receive dental arches.

U.S. Pat. No. 4,810,192 by Williams discloses a two stage intra oral protective system, stage one comprising a mandibular repositioning apparatus having a biteplate and stage two comprising a mouth guard. Stage one engages the posterior teeth of the mandible.

The instant art engages no posterior teeth and does not comprise a mouth guard or a bite plate.

U.S. Pat. No. 5,173,148 by Summer recites a dental splint covering lower teeth and having a moldable material whereby impressions of teeth are taken.

The instant art engages only occlusal surfaces of anterior lower teeth and comprise no dental impression taking element.

U.S. Pat. No. 5,066,226 by Summer discloses a telescopic oral appliance having extensible-retractable positioning device and attached to upper and lower teeth.

The instant art attaches only to upper anterior teeth and has no extensible-retractable element.

U.S. Pat. No. 6,978,786 B2 by Sabbagh discloses a device having pads placed on the occlusal surfaces of posterior teeth, said pads being fluid filled and having tubes for inter-pad fluid transfer.

The instant art has no pads, fluid filled or otherwise, engaging posterior teeth, and no tubes for fluid transfer between pads.

U.S. Pat. No. 5,368,477 by Neely teaches a dental device having a disposable cushion portion attached to head portions.

The instant art has no disposable cushions.

U.S. Pat. No. 4,211,008 by Lerman teaches a dental device having occlusal portions interconnected at their forward ends by a labial portion. The occlusal portions form fluid filled cells, which are interconnected to allow fluid transfer, placed between posterior teeth.

The instant art has no fluid filled cushions, has no transfer of fluid between cushions, and has no elements placed between posterior teeth.

U.S. Pat. No. 6,237,601 B1 by Kittelson et al. discloses a dental appliance having an occlusal posterior pad having four layers and an adjustable arch molded to the palate.

The instant art has no element engaging occlusal surfaces of posterior teeth, no element communicating with the palate, and does not teach multi-layer construction.

U.S. Pat. No. 5,879,155 by Kittelson discloses an adjustable dental appliance having an occlusal posterior pad for each side of posterior teeth.

The instant art engages no posterior teeth.

U.S. Pat. No. 5,584,687 by Sullivan et al. teaches a dental appliance having an occlusal posterior pad for each side of posterior teeth and an arch connecting the pads.

The instant art has no elements engaging posterior teeth.

U.S. Pat. No. 7,234,467 B2 by Ball teaches a dental splint having a portion molded to fit over incisors and an opposing surface having a groove to receive teeth of the opposing dental arch.

The instant art engages only lingual surfaces of incisors and need not comprise structure to receive opposing teeth, U.S. Pat. No. 7,730,891 B2 by Lamberg teaches a dental appliance attachable to the maxillary anterior teeth with retention means for said maxillary teeth and a protrusive element depending from the main body and a lingual spacer extending posteriorly from the anterior mandibular arch with an aspect parallel to an arc defined by the motion of the incisal edges of the lower teeth as they rotate around the condylar hinge axis.

The instant art engages only lingual surfaces of the anterior maxillary teeth, has no lingual spacer, no protrusive element depending from a main body, and no element having contour conforming to condylar motion.

Japan Abstract JP 2009082670 (A) by Masuhiro teaches a dental implement inserted between upper and lower anterior teeth to create an interval therebetween. It is held in place by element which engages the outer surfaces of the front teeth and comprises a bio-feedback device.

The instant art engages only lingual surfaces of upper anterior teeth, maintains no interval between upper and lower teeth, and has no bio-feedback means.

The instant art is less complex, lighter, less expensive, more comfortable to wear than existing technologies, and can be worn for longer periods than previous technologies. Further, the instant art is less obvious in the mouth than extant art and does not interfere with speech or breathing.

Therefore, for at least the above reasons, the instant art is a needed and significant advancement in the art of temporomandibular joint disorder alleviation.

BRIEF SUMMARY OF THE INVENTION

The primary object of the invention is to provide a temporomandibular joint disorder alleviation device that is comfortable to wear.

Another object of the invention is to avoid completely covering any tooth, and avoiding contact with the facial surfaces of teeth, and, in some embodiments occlusal surfaces of upper teeth.

Another object of the invention is to avoid requiring communication with every tooth.

A further object of the invention is to allow movement of the lower jaw relative to the upper jaw.

Yet another object of the invention is attachment only to upper jaw teeth.

Still yet another object of the invention is simple and inexpensive fabrication.

Another object of the invention is quick and simple customization for individual patients.

Still another object of the invention is to not interfere with breathing.

Yet another object of the invention is to not interfere with speech.

Still yet another object of the invention is to be un-obvious when worn in the mouth.

Other objects and advantages of the present invention will become apparent from the following descriptions, taken in connection with the accompanying drawings, wherein, by way of illustration and example, an embodiment of the present invention is disclosed.

In accordance with a preferred embodiment of the invention, there is disclosed a machine for mitigation of temporomandibular joint disorder comprising: lingual tooth surface contact surface, hard palate conformity, anterior pad, and pad wings.

BRIEF DESCRIPTION OF THE DRAWINGS

The drawings constitute a part of this specification and include exemplary embodiments to the invention, which may be embodied in various forms. It is to be understood that in some instances various aspects of the invention may be shown exaggerated or enlarged to facilitate an understanding of the invention.

LIST OF NUMBERED ELEMENTS

Figure 1:
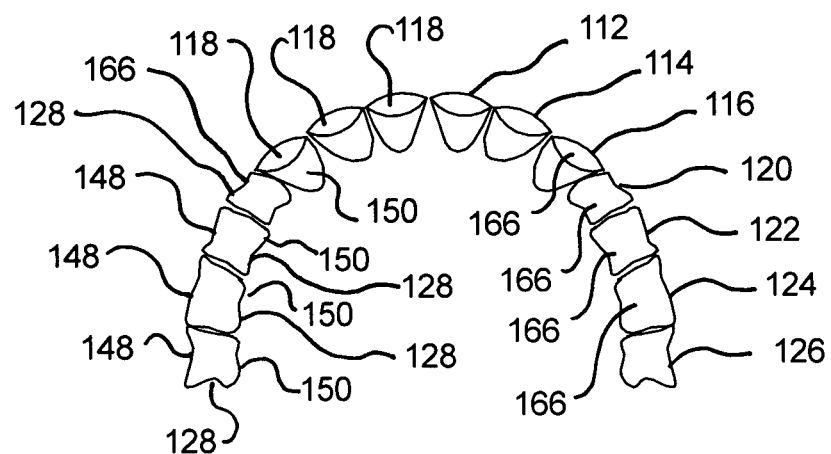
FIG. 1 is a top view of normal dentition.

110. Temporomandibular joint disorder mitigation device
112 Central incisor 114 Lateral incisor
116 Cuspid
118 Anterior teeth
120 First bicuspid
122 Second bicuspid
124 First molar
126 Second molar
128 Posterior tooth
130 Lower jaw
132 Upper jaw
134 Middle section
136 Ascending ramus
138 Coronoid process
140 Condyle
142 Meniscus
144 Articular surface of temporal bone
146 Hard palate
148 Facial tooth surface
150 Lingual tooth surface
152 Lingual tooth surface contact surface
154 Ball clasp
156 Hard palate conformity
158 Lingual tooth surface conformity
160 Tooth clearance
162 Anterior pad
164 Pad wings
166 Occlusal surface
167 Incisal surface
168 U-shape or arch
170 Middle portion
172 Top surface
174 Bottom surface
176 Incline
178 Surface decline
Direction arrow A
Direction arrow B
Direction arrow C
Direction arrow D

DETAILED DESCRIPTION OF THE PREFERRED EMBODIMENTS

Detailed descriptions of the preferred embodiment are provided herein. It is to be understood, however, that the present invention may be embodied in various forms. Therefore, specific details disclosed herein are not to be interpreted as limiting, but rather as a basis for the claims and as a representative basis for teaching one skilled in the art to employ the present invention in virtually any appropriately detailed system, structure or manner.

The instant art deals with the proper function of, and modification of or adjustment of the temporomandibular joint functions. Said functions and the anatomy of said joint, as well as pathological anomalies thereof, are well known in the art. Therefore they are not presented in stringent detail but only to the point necessary for teaching the use of the instant art.

The instant art is depicted in relation to dentention of the human mouth but is not intended to be limited thereto. Also, because the instant art does not teach involvement of the third molars, wisdom teeth, such are not depicted in any drawings. Further, it is well known that particular teeth and portions thereof might have more than one name; therefore, for the purposes of these specification and claims, the teeth and portions thereof are named as in FIG. 1 wherein the teeth are termed central incisor (112), lateral incisor (114), cuspid (116), and wherein said teeth are referred to as anterior teeth (118), first bicuspid (120), second bicuspid (122), first molar (124), and second molar (126), and wherein said teeth are referred to as posterior teeth (128). The surfaces of teeth nearest the tongue are referred to as lingual surfaces (150), the surfaces of teeth opposite the lingual surfaces (150) are referred to as facial surfaces (148), and the surfaces of teeth which may contact or act in concert with corresponding surfaces on teeth of an opposing dental arch are referred to as occlusal surfaces (166) or incisal surfaces (167). Occlusal surfaces, as is well known in the art, comprise an occlusal plane, said occlusal plane being a well understood, familiar, easily determinable feature to one familiar with the dental arts. When used in reference to position or direction, the term "anterior" means toward or proximal the front of the mouth, and the term "posterior" means toward or proximal the rear of the mouth.

Those well versed in the art will readily appreciate that numbered elements of FIG. 1 apply accurately to either dentention of the upper jaw or dentention of the lower jaw. The dentention, either upper or lower, intended in the specification and claims is obvious from the context.

Figure 2:
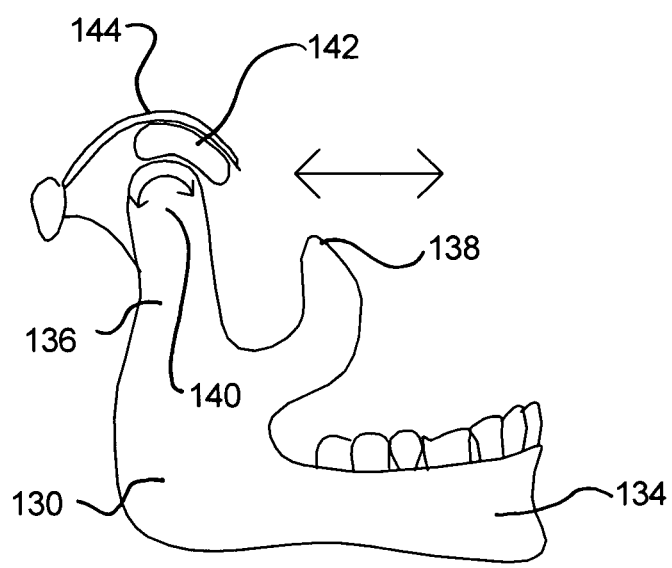
FIG. 2 is a side view of the temporomandibular joint and mandible.

FIG. 2 shows that the lower jaw or mandible (130) comprises a U-shaped middle section (134) which supports dentention, an ascending ramus (136) which rises substantially perpendicularly from the middle section (134) and divides into two branches, the most posterior ending in a rounded condyle (140) and the most anterior comprising a coronoid process (138) which serves as an anchor point for muscles affecting jaw movement. The condyle (140) communicates with the skull by means of a meniscus (142) interposed between said condyle (140) and an articular surface of the temporal bone (144). The condyle (140) may rotate, as indicated by curved, double-pointed arrow, thus allowing movement of the lower jaw (130) to affect opening and/or closing of the mouth. The condyle (140) may also translate, that is move forwards and/or backwards, as indicated by horizontal, double-pointed arrow.

Figure 3:
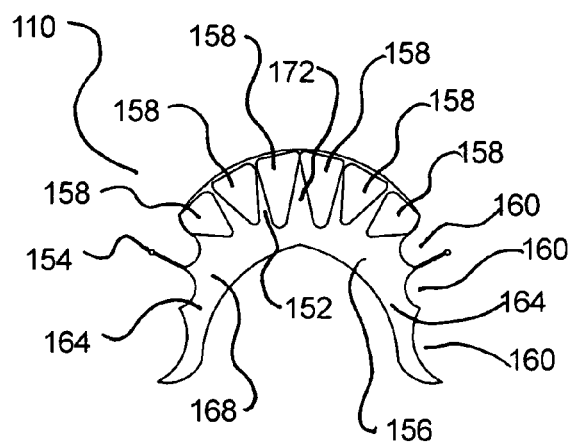
FIG. 3 is a top view of the temporomandibular joint disorder mitigation device.
Figure 4:
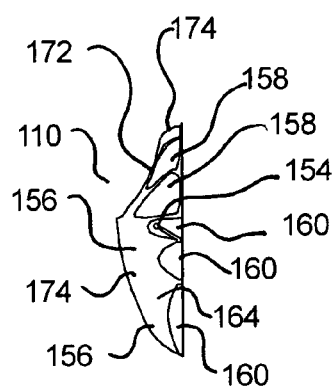
FIG. 4 is a side view of the temporomandibular joint disorder mitigation device.
Figure 5:
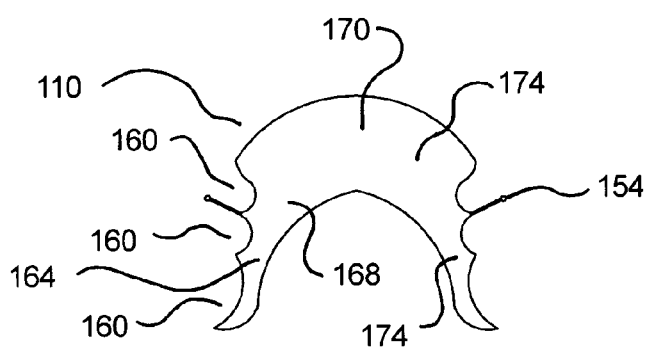
FIG. 5 is a bottom view of the temporomandibular joint disorder mitigation device.

FIG. 3, FIG. 4, and FIG. 5 show the temporomandibular joint disorder mitigation device (110) which is conformed in essentially a U-shape, or arch, (168), said U-shape or arch (168) having an anterior middle portion (170). Extending posteriorly from opposite sides of the anterior middle portion (170) are pad wings (164). The whole (110) is contoured to communicate with an upper jaw and dentention thereof. The device (110) comprises a top surface, seen in FIG. 3 and FIG. 4, and a bottom surface (174) shown in FIG. 5.

The device (110) may comprise any of well known materials commonly used in the art to fabricate sundry types of dental appliances worn either temporarily or permanently. Said material may comprise suitable flexibility, pliability, or resiliency as deemed necessary by one well versed in the art. The device (110) may comprise smooth or textured surfaces, and the device (110) may comprise material having transparency, color or pigmentation, translucence, and/or opacity. Thus, maximum comfort, minimum stress on anatomical elements interfacing with the device, and or maximum unobtrusiveness of the device (110) may be achieved.

The top surface (172) of the device (110) comprises a lingual tooth surface contact surface (152) which may further comprise one or more lingual tooth surface conformities (158), which by means well known in the art, may be configured to communicate essentially contiguously with the lingual surface (150), or a portion thereof, of particular teeth. In FIG. 1, six lingual tooth surface conformities (158) are noted which conform to the lingual tooth surfaces (150) of the anterior teeth (118). However, the device (110) will function satisfactorily if configured to contact the lingual tooth surface (150) of fewer anterior teeth (118), as in FIGS. 7A and 7D wherein neither the lingual tooth surfaces (150) of the cuspids (116) nor the lingual tooth surface (150) of teeth other than and/or in addition to the anterior teeth (118) touch the device. Or, it can be configured as in FIG. 7B wherein the lingual tooth surfaces (150) of the first bicuspids also communicate with the device (110).

In FIG. 3 and FIG. 4 is seen a hard palate conformity (156) which comprises the top surface (172) of the pad wings (164) and that portion of the top surface (172) of the device middle portion (170) posterior of the lingual tooth surface conformity (158). Thus, it may be readily appreciated that the hard palate conformity (156) comprises an unbroken arch.

Figure 7:
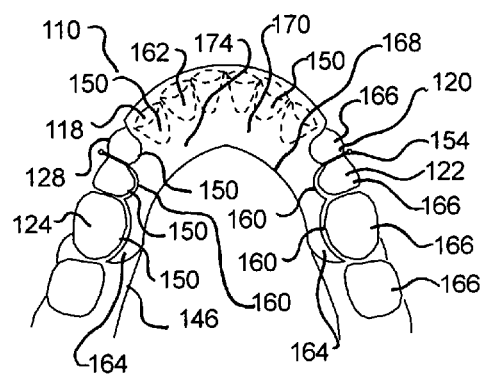
FIG. 7 is a view of the temporomandibular joint disorder mitigation device seen from the bottom communicating with the upper jaw and teeth.
Figure 7A:
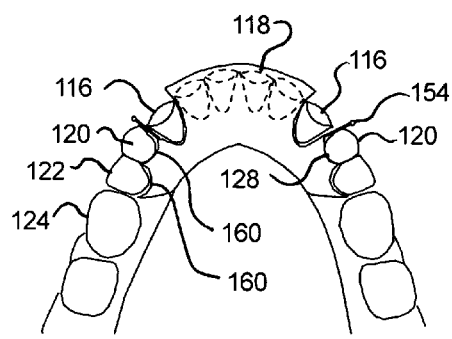
FIG. 7A is a view of an alternate embodiment of the temporomandibular joint disorder mitigation device seen from the bottom communicating with the upper jaw and teeth.
Figure 7B:
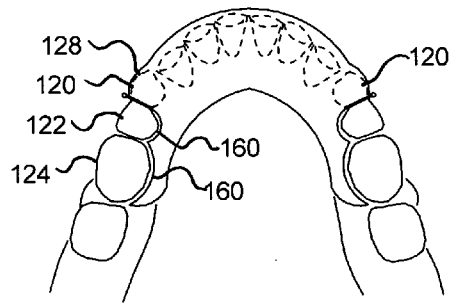
FIG. 7B is a view of an alternate embodiment of the temporomandibular joint disorder mitigation device seen from the bottom communicating with the upper jaw and teeth.
Figure 7C:
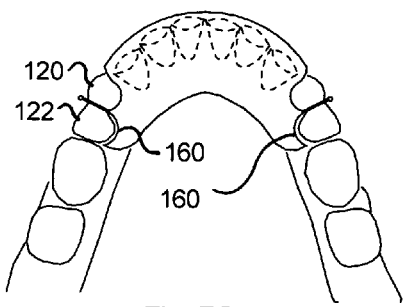
FIG. 7C is a view of an alternate embodiment of the temporomandibular joint disorder mitigation device seen from the bottom communicating with the upper jaw and teeth.
Figure 7D:
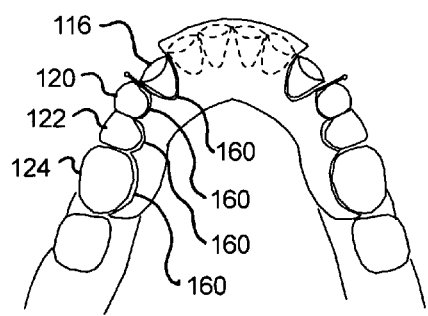
FIG. 7D is a view of an alternate embodiment of the temporomandibular joint disorder mitigation device seen from the bottom communicating with the upper jaw and teeth.

Though FIG. 3, FIG. 4, FIG. 5, and FIG. 7 depict the device (110) as comprising tooth clearances (160) for the first bicuspids (120), second bicuspids (122) and first molars (124), tooth clearances for more or fewer teeth may be provided, as in FIG. 7B wherein clearances (160) for the second bicuspids (122) and first molars (124) are provided, FIG. 7C wherein clearances (160) for the first bicuspids (120) and second bicuspids (122) are provided, and FIG. 7D wherein clearances (160) for the cuspids (116), first bicuspids (120), second bicuspids (122), and first molars (124) are provided, rendering the instant art (110), as simple, small, unobtrusive, and comfortable as possible.

FIG. 3, FIG. 4, and FIG. 5 show that the pad wings (164) comprise one or more tooth clearances (160) and one or more ball clasps (154). The ball clasp (154) is an artifice well known in the dental arts to anchor or secure a device in the mouth. Therefore its structure and function will not be detailed.

In FIG. 7, the ball clasp (154) is configured to extend from the pad wing (164) between the first bicuspid (120) and second bicuspid (122). Those well versed in the art will also readily appreciate that the ball clasp (154) may serve as a handle to facilitate insertion and/or removal of the device (110). However, the device (110) may function satisfactorily if the ball clasp (154) is otherwise positioned, as in FIG. 7A or 7B wherein the ball clasps (154) are positioned between the cuspids (116) and the first bicuspids (120).

Figure 8:
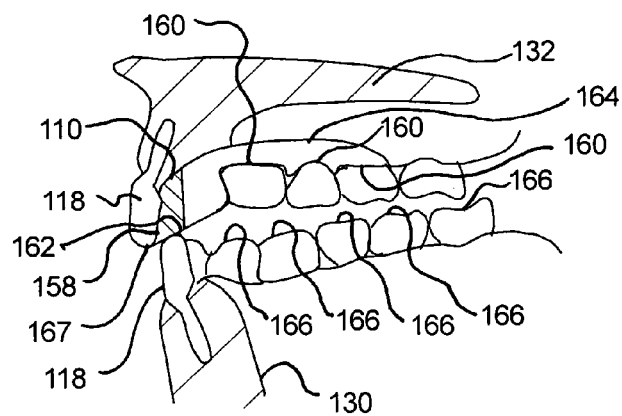
FIG. 8 is a side cross sectional view of temporomandibular joint disorder mitigation device in operative communication with human dentention.

Referring to FIG. 8, the device may also function satisfactorily without the ball clasps (154), or with alternate methods of oral appliance securement substituted. In example, the conformity of the top surfaces of the device with the hard palate (146) and the lingual surfaces (150) of anterior teeth (118), either alone or in combination with force applied by the lower jaw anterior tooth (118) contact with the anterior pad (132) may provide sufficient friction to retain the device (110) in operative position.

FIG. 7 also shows, that in operative position, the device (110) communicates substantially contiguously with the lingual and occlusal surfaces of the anterior teeth (118) and the hard palate (146). Additionally, it may be noted that the posterior teeth (128), particularly the first bicuspid (120), second bicuspid (122), and first molar (124) do not communicate with the pad wings (164), due to the presence of the tooth clearances (160). Also shown is an anterior pad (162) comprising the bottom surface (174) of the middle portion (170) of the arch (168) of the device (110). As shown in FIG. 8, the device (110) can but need not communicate with the occlusal surfaces (166) of the posterior teeth (128), or the incisal surfaces (167) of the anterior teeth (118).

In addition, it may be noted that function of the device (110) does not require it to be in communication with the roof of the mouth or soft palate.

Figure 6:
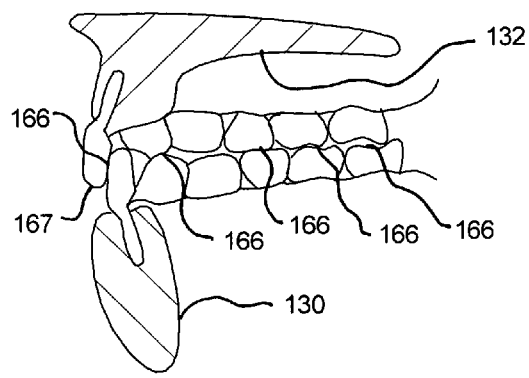
FIG. 6 is a side cross sectional view of human dentention showing non-appliance adjusted occlusion.

FIG. 6 shows that the upper jaw (132) and the lower jaw or mandible (130) may contiguously interface at occlusal surfaces (166). Thus, occasion may be created for temporomandibular joint disorder causing undesirable events or conditions, in example bruxism or forward thrusting of the lower jaw (130).

FIG. 8 shows that when the device (110) is disposed in operative position, the anterior pad (162) is interposed between the upper jaw (132) anterior teeth (118) and the lower jaw (130) anterior teeth (118) to serve the function of limiting the range of upward vertical extension of the lower jaw (130), effectively blocking occlusion of occlusal surfaces (166) of posterior teeth (128). Also noted is that the anterior teeth (118) are free to contact and move about on the surface of the anterior pad (162).

In addition, the flexibility, pliability, and/or resiliency of the material comprising the device may serve to cushion the contact between the anterior pad (162) and the lower jaw anterior teeth (118). Noted also in FIG. 8 is that the anterior pad is disposed essentially parallel to the occlusal plane of the anterior teeth (118).

In this manner, bruxism and its attendant damage causing stress on the temporomandibular joint are mitigated. This also allows opportunity for, any previous temporomandibular joint damage is given to heal. Further, the previously mentioned temporomandibular joint disorder associated symptoms, especially the pains in various localities, may be significantly alleviated if not altogether eliminated.

Figure 9:
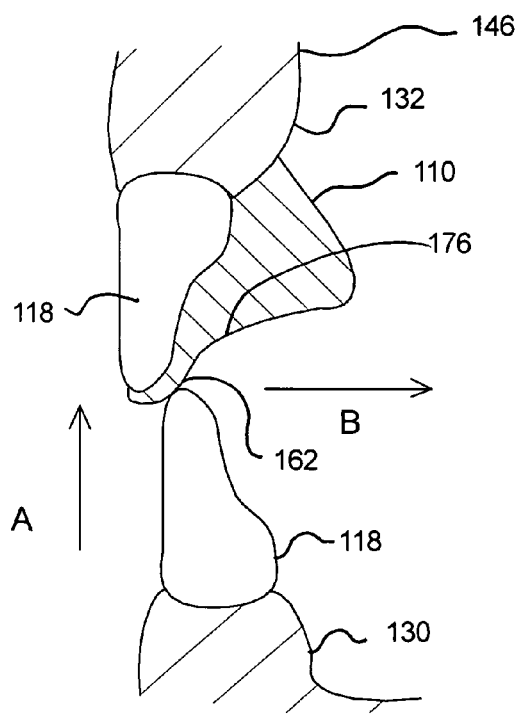
FIG. 9 is a side cross sectional view of an alternate embodiment of temporomandibular joint disorder mitigation device in operative communication with human dentention.

Referring to FIG. 9, one may readily appreciate that movement of the anterior teeth (118) relative the anterior pad (162) may be freely accomplished by translational movement of the lower jaw (130).

FIG. 9 shows that the anterior pad (162) may be configured so as to comprise an incline (176) from anterior to posterior. So configured, when the lower anterior tooth is thrust against the anterior pad (162) in direction A, as indicated by arrow A, a force B, as indicated by arrow B, essentially toward the posterior, will result. Thus, as the jaw (130) closes, it is naturally forced toward the posterior.

In this manner, forward thrusting of the lower jaw (130) and its attendant damage causing stress on the temporomandibular joint are mitigated. Thus, any previous temporomandibular joint damage is given opportunity to heal, and the previously mentioned temporomandibular joint disorder associated symptoms, especially the pains in various localities, may be significantly alleviated if not altogether eliminated.

Figure 10:
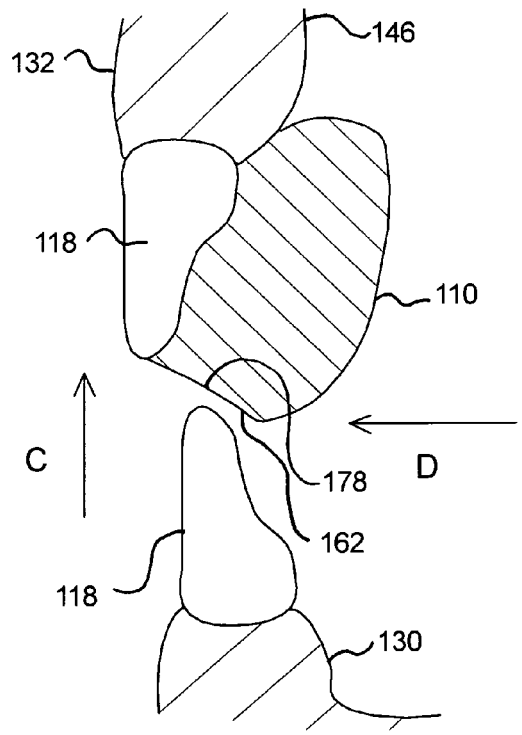
FIG. 10 is a side cross sectional view of an alternate embodiment of temporomandibular joint disorder mitigation device in operative communication with human dentention.

Although the device (110) is depicted as having an anterior pad (162) extending essentially horizontally or at an incline from anterior to posterior, the instant art is not intended to be thusly limited. In particular, an anterior pad (162), as in FIG. 10, may comprise a surface declining (178) from anterior to posterior, thusly creating a force in direction C, toward the anterior, as indicated by arrow C, when force in direction D, as indicated by arrow D, causes lower jaw (130) anterior teeth (118) to encounter the anterior pad (162). Such disposition could be utilized for a patient with an under bite.

So configured, one may readily appreciate that movement of the anterior teeth (118) relative the anterior pad (162) may be freely accomplished by voluntary forward translational movement of the lower jaw (130

While the invention is described in connection with a preferred embodiment, it is not intended to limit the scope of the invention to the particular form set forth, but on the contrary, it is intended to cover such alternatives, modifications, and equivalents as may be included within the spirit and scope of the invention as defined by the appended claims.

What is claimed is:

1. A device for mitigation of temporomandibular joint disorder comprising:
   a middle portion having a top surface and a bottom surface, the top surface being configured to communicate with lingual surfaces of four or more anterior upper jaw teeth and the hard palate, the bottom surface of the middle portion being comprised of an anterior pad that is configured such that movement of the anterior lower jaw teeth relative to the anterior pad can be freely accomplished by translational movement of the lower jaw, the anterior pad having a thickness such that only the anterior lower jaw teeth contact the anterior pad to prohibit occlusion of the posterior teeth; and
   pad wings extending posteriorly from opposite extremes of the middle portion, said pad wings having a top surface configured to communicate with the hard palate of the upper jaw structure and tooth clearances for one or more posterior teeth;
   wherein the device does not comprise a protrusive element extending from the bottom surface of the middle portion and that is configured to engage lingual surfaces of the anterior lower jaw teeth.

2. A device as in claim 1, further-comprising one or more ball clasps that extend from the middle portion.

3. A device as in claim 1, wherein the anterior pad comprises a contour that inclines from anterior to posterior.

4. A device as in claim 1, wherein the anterior pad comprises a contour that declines from anterior to posterior.

5. A device as in claim 1, wherein said top surface is configured to communicate with at least one occlusal surface of at least one anterior upper jaw tooth.

6. A device as in claim 1, wherein a portion of the device that engages the anterior upper jaw teeth is configured to only engage the lingual surfaces of the anterior upper jaw teeth.

7. A device as in claim 1, wherein the anterior pad is configured such that movement of the anterior lower jaw teeth relative to the anterior pad can be freely accomplished by voluntary forward translational movement of the lower jaw.

8. The device of claim 1, wherein the device is conformed substantially in a U-shape, and wherein the device does not communicate with the soft palate.

9. The device of claim 1, wherein the device does not communicate with the posterior teeth.

10. A device, comprising:
    a main U-shaped body configured for placement in the upper jaw of a subject that includes an anterior central portion and two posteriorly extending wing portions;
    a top surface of each of the wing portions being configured to communicate with the hard palate;
    a top surface of the anterior central portion being configured to communicate with the hard palate and lingual surfaces of four or more anterior upper jaw teeth; and
    a bottom surface of the anterior central portion having an anterior pad, the bottom surface of anterior pad being configured such that voluntary forward translational movement of the lower jaw teeth relative to the device can be freely accomplished, and the anterior pad having a thickness such when the jaw of the subject is closed only the anterior lower jaw teeth contact the device at a bottom surface of the anterior pad;
    wherein the device does not comprise a protrusive element extending from the bottom surface of the anterior central portion and that is configured to engage lingual surfaces of the anterior lower jaw teeth.

11. A device as in claim 10, wherein the device does not contact the soft palate, the posterior teeth, or both.

12. A device as in claim 10, wherein a portion of the device that communicates with the anterior upper jaw teeth only engages the lingual surfaces of the anterior upper jaw teeth.

13. A device as in claim 10, further comprising one or more ball clasps that extend from edges of the device and being configured to engage at least one upper jaw tooth.

14. A device for mitigation of temporomandibular joint disorder comprising:
    a middle portion having a top surface and a bottom surface, the top surface being configured to communicate with lingual surfaces of four or more anterior upper jaw teeth and the hard palate, the bottom surface of the middle portion being comprised of an anterior pad that is configured such that movement of the anterior lower jaw teeth relative to the anterior pad can be freely accomplished by translational movement of the lower jaw, the anterior pad having a thickness such that only the anterior lower jaw teeth contact the anterior pad to prohibit occlusion of the posterior teeth; and
    pad wings extending posteriorly from opposite extremes of the middle portion, said pad wings having a top surface configured to communicate with the hard palate of the upper jaw structure and tooth clearances for one or more posterior teeth;
    wherein a portion of the device that engages the anterior upper jaw teeth is configured to only engage the lingual surfaces of the anterior upper jaw teeth;
    wherein the device does not comprise a protrusive element extending from the bottom surface of the middle portion and that is configured to engage lingual surfaces of the anterior lower jaw teeth.

* * * * *